United States Patent [19]

Bader et al.

[11] Patent Number: 5,424,472
[45] Date of Patent: Jun. 13, 1995

[54] METHOD OF MANUFACTURING A (METH)ACRYLOYLTHIO COMPOUND

[75] Inventors: Martina Bader, Griesheim; Patrik Hartmann, Buettelborn; Gerhard Schwinn, Dieburg, all of Germany

[73] Assignee: Roehm GmbH Chemische Fabrik Patentabteilung, Darmstadt, Germany

[21] Appl. No.: 134,739

[22] Filed: Oct. 12, 1993

[30] Foreign Application Priority Data

Oct. 10, 1992 [DE] Germany .................. 42 34 257.0

[51] Int. Cl.$^6$ .................................. C07C 327/22
[52] U.S. Cl. ...................... 558/250; 558/251; 558/252; 558/255; 558/257
[58] Field of Search .................. 558/250, 257

[56] References Cited

U.S. PATENT DOCUMENTS

| | | | |
|---|---|---|---|
| 2,445,142 | 7/1948 | Himel | 558/250 |
| 2,475,246 | 7/1949 | Mikeska | 558/257 X |
| 2,550,141 | 4/1951 | Doumani et al. | 558/250 |
| 3,061,612 | 10/1962 | Toland | 558/250 X |
| 3,402,194 | 9/1968 | Schleppnik | 558/257 |
| 3,929,852 | 12/1975 | Kydonieus et al. | 558/250 |
| 4,606,864 | 8/1986 | Warren | 558/257 |
| 4,654,431 | 3/1987 | DeBoer | 558/257 |

OTHER PUBLICATIONS

Patent Abstracts of Japan, vol. 16, No. 71 (C-913), Feb. 21, 1992, AN 129857c, JP-A-03 264 549, Nov. 25, 1991.

*Primary Examiner*—Mary C. Lee
*Assistant Examiner*—Michael G. Ambrose
*Attorney, Agent, or Firm*—Oblon, Spivak, McClelland, Maier, & Neustadt

[57] ABSTRACT

The invention relates to a method of producing (meth)acryloylthio esters of general formula I

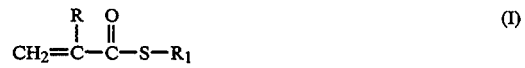

where R represents hydrogen or methyl, and
R$_1$ represents a phenyl group, a substituted phenyl group, a C$_{1-24}$ alkyl group, a substituted C$_{1-24}$ alkyl group, a cyclic C$_{3-24}$ alkyl group;

comprising reacting (meth)acrylic acid anhydride (formula II)

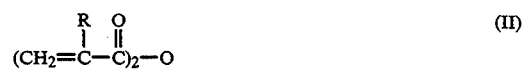

where R represents hydrogen or methyl, with at least the stoichiometric amount with a thiol or thiolate of formula III

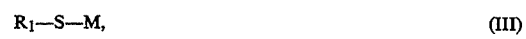

where M represents hydrogen or a metal cation, and R$_1$ is defined as above.

6 Claims, No Drawings

METHOD OF MANUFACTURING A (METH)ACRYLOYLTHIO COMPOUND

BACKGROUND OF THE INVENTION

1. Field Of the Invention

The invention relates to a method of producing a (meth)acryloylthio compound, starting from (meth)acrylic acid anhydride.

2. Discussion of the Background

The preparation of esters of thiocarboxylic acids, which esters are categorized as "active esters", may be regarded as a process starting with reactive carboxylic acid derivatives. Thus, e.g., hitherto (meth)acryloylthio esters have been produced preferably from the corresponding carboxylic acid halides (see Koton, M. M., et al., 1956 Zh. ObShch. Khim. 26, 475–6; CA 50:13815; JP 2-229,808 and JP 3-011,054). The synthesis of bis(meth)acryloylthio) compounds from 3-chloro-(2-methyl)-propanoic acid chloride and dithiols is the subject of JP 02-172,969. In JP 02-003,675, the preparation of (meth)acryloylthio esters from (meth)acryloyl chloride with phase transfer catalyst is described. Bis{(meth)acryloylthio}compounds may also be produced by this general method, as described in EP-A 273,661.

Reaction of (meth)acrylic acid halides gives rise to a number of problems. Thus, e.g., (meth)acrylic acid chloride has a pungent odor, fumes when exposed to air, and is a potent eye irritant; further, it has a tendency to homopolymerize. Acryloyl chloride is readily volatilized, is a strong irritant to mucous membranes, and readily homopolymerizes in light. (See Rauch-Puntigam, H., and Voelker, Th., 1967, "Acryl- und Methacrylverbindungen", pub. Springer-Verlag, of Berlin, Heidelberg, and New York, pp. 19 and 43.) Accordingly the problem is presented of devising a method of producing esters of (meth)acrylic acid and aromatic or aliphatic thiols which method does not employ acid halides. A consideration is that as the activation of the carbonyl function is decreased the probability of reaction at the double bond is increased, e.g., by addition of nucleophiles, or addition polymerization.

When thiols are reacted with (meth)acrylic acid derivatives having a decreased carbonyl reactivity than that of an acid halides, one must take into account 1,4-addition of the thiol to the activated double bond. (See Houben-Weyl, 1955, "Methoden der organischen Chemie" 4th Ed Vol IX, pub. Georg Thieme-Verlag, pp. 124–125.) Molecules with two (activated) double bonds in the molecule, such as, e.g., (meth)acrylic acid anhydride, have enhanced addition capability, so that reaction to form the thiolic ester would not be expected. Counter to expectation, however, it has been discovered, in connection with the present invention, that (meth)acryloylthio compounds can be produced by reacting a thiol with (meth)acrylic acid anhydride.

SUMMARY OF THE INVENTION

Accordingly, the invention concerns a method of producing (meth)acryloylthio esters of the formula I

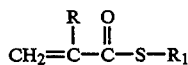     (I)

where R represents hydrogen or methyl, and
R$_1$ represents a phenyl group, substituted phenyl group, a C$_{1-24}$ alkyl group, preferably C$_{1-12}$ alkyl, a substituted C$_{1-24}$ alkyl group, a C$_{3-24}$ cyclic alkyl group; comprising reacting a (meth)acrylic acid anhydride (formula II)

     (II)

where
R represents hydrogen or methyl,
with at least the stoichiometric amount of a thiol or thiolate of formula III

     (III)

where
M represents hydrogen or a metal, particularly an alkali cation, and
R$_1$ is defined as above.

DETAILED DESCRIPTION OF THE PREFERRERD EMBODIMENTS

Preferably, the reaction is carried out in aqueous medium, but the anhydride (formula II) is employed in general in a suitable inert organic solvent L which is preferrably is not water-miscible, to create a two-phase system. Preferably the reaction is carried out in the presence of a base, particularly if the thiol is employed in free form (with M being hydrogen). The preferred base is alkali hydroxide or alkali carbonate, particularly with sodium or potassium as the cation. Even where M represents a metal cation, sodium and potassium are preferred.

The preparation of the starting compound of formula II, (meth)acrylic acid anhydride, is reported in Rauch-Puntigam, H., and Voelker, Th., loc.cit., 19, 20, 43, 44 and can be prepared by conventional methods known to those of ordinary skill in the art. As acid anhydrides with additional activation of the double bond, these liquids decompose when acted on by water, and they have a pronounced tendency to polymerize, thereby requiring careful handling. In handling the anhydrides, the irritating action of their vapors on mucous membranes must also be taken into account.

The thiols of formula III are also reported (see Houben-Weyl, loc.cit,, Vol. IX, 3–48) and can be prepared by conventional methods known to those of ordinary skill in the art. Particular candidates for such thiols which might be mentioned are alkylthiols such as propanethiol, butanethiol, pentanethiol, hexanethiol, heptanethiol, octanethiol, nonanethiol, decanethiol, and dodecanethiol; also (thio)ether mercaptans such as, e.g., 2,2'-dimercapto-diethyl ether and 2,2'-dimercapto-diethyl sulfide; substituted alkylthiols such as ethyl 3-mercaptopropanoate and ethyl thioglycolate; or aromatic compounds such as phenylethanethiol and thiophenol.

Candidates for R$_1$ of a substituted type are preferably moieties with
carboxyl groups, which groups may be esterified with a C$_{1-6}$ alcohol,
a C$_{1-4}$ alkyl group, or
halogen, particularly fluorine, chlorine, and bromine.

The reaction between compounds II and III takes place in the stoichiometric 1:1 molar ratio (i.e. 1 mole of thiol per mole of acid anhydride), but it is advantageous to provide the acid anhydride II in a certain excess, e.g.

an excess over the stoichiometrically required amount of III by a factor of 0.05–0.5.

Examples of suitable inert solvents L in which the compound II is preferably employed are, e.g., aromatic hydrocarbons such as toluene and xylene, and ethers such as methyl t-butyl ether (MTBE).

It is also advisable to stabilize the anhydride II by addition of a polymerization inhibitor, e.g. from the class of sterically hindered phenols, e.g. 4-methyl-2,6-di-t-butylphenol, 2,4-dimethyl-6-t-butylphenol, or t-butylpyrocatechol; or quinone compounds such as hydroquinone monomethyl ether, etc., generally in amounts of 0.01–0.2 wt. % (based on the weight of the polymerizable material).

The reaction may be carried out, e.g., as follows: The anhydride II in the solvent L is charged to a reaction vessel equipped with a stirrer. An amount of solvent equal to 5–10 times the amount of II (by weight) is suggested. Preferably the mixture is cooled with ice cooling, and the thiol III, which may be, e.g., in c. 4 times its weight of aqueous alkali solution (said aqueous alkali solution comprising e.g.c. 10% sodium hydroxide), is added dropwise over a period of time, e.g.c. 60 min. In general, a pH in the range 7–10 is maintained. Following the dropwise addition, stirring is continued for some time, e.g.c. 3 hr, preferably at temperatures above room temperature, e.g. 40° C. Then the organic phase is separated out by means of a separatory funnel and generally is washed once with water, once with an aqueous alkali solution, e.g. of pH 12, to remove (meth)acrylic acid which has formed, and once again with water. Advantageously the material is dried over a suitable drying agent, e.g. sodium sulfate, and the solvent is removed, e.g. under reduced pressure in a rotary evaporator. If the recovered raw product still does not meet the requirements, advantageously it is refined to yield pure product of formula I by distillation. under high vacuum. The raw product may contain a small proportion of the 1,4-addition product of the thiol and the thiolic ester; which can be removed by distillation.

The inventively produced monomers may be processed to provide, e.g., transparent, high refractive index plastics, (i.e. RI > 1.589). Such plastics may in turn be processed to form numerous optical devices and articles, e.g. lenses for eyeglass lens applications, etc.

Having generally described this invention, a further understanding can be obtained by reference to certain specific examples which are provided herein for purposes of illustration only and are not intended to be limiting unless otherwise specified.

The following Examples serve to illustrate the invention.

Examples

Example 1: Production of methacryloylthiohexane

A solution of 35 g hexanethiol in 140 mL 10% aqueous sodium hydroxide solution was added dropwise under ice cooling to a solution of 49.9 g methacrylic acid anhydride (stabilized with 1,000 ppm 4-methyl-2,6-di-t-butylphenol) in 450 ml MTBE. Following completion of the dropwise addition, the mixture was stirred 3 hr at 40° C. The organic phase was separated out and washed with water. After drying with sodium sulfate and removal of the solvent, the material was distilled to yield methacryloylthiohexane (boiling point 65° C. at 0.3 mbar). Yield: 83% of theoretical. The structure was confirmed by NMR, GC-MS, and IR.

Example 2: Production of methacryloylthiobenzene

A solution of 55.1 g thiophenol and 20.4 g NaOH in 80 mL water was added under ice cooling to a solution of 77 g methacrylic acid anhydride (stabilized with 1,000 ppm 4-methyl-2,6-di-t-butylphenol) in 400 ml MTBE. Following completion of the dropwise addition, the mixture was stirred 3 hr at 40° C. The organic phase was separated out and washed with water. After drying, the raw ester solution was distilled (b.p. 70°–72° C. at 0.5 mbar). Methacryloylthiobenzene was obtained, with purity > 98% according to GC, in yield 80% of theoretical.

Example 3: Production of methacryloylthiomethane (thiomethacrylic acid S-methyl ester)

25 g gaseous methyl mercaptan was introduced to a mixture of 84.7 g methacrylic acid anhydride, 480 ml methyl t-butyl ether, 240 mL 10% aqueous NaOH solution, and 85 mg 4-methyl-2,6-di-t-butylphenol, under ice cooling. Following completion of the introduction of the methyl mercaptan, the mixture was stirred 4 hr at 40° C. The mixture was cooled and the organic phase was separated out, washed with water, and dried with sodium sulfate. After distillation, 21.4 g methacryloylthiomethane was obtained (b.p. 46°–50° C. at 13 mbar; yield 36% of theoretical).

Example 4: Production of methacryloylthio-3-thiobutane (thiomethacrylic acid S-3-thiobutyl ester)

A solution of 76 g 3-thiobutyl mercaptan in 500 ml 6% aqueous NaOH solution was added dropwise under cooling to a solution of 116 g methacrylic acid anhydride (stabilized with 116 mg 4-methyl-2,6-di-t-butylphenol) in 800 ml MTBE. After completion of the dropwise addition, the mixture was stirred 4 hr at 40° C. The organic phase was separated out, washed with water, and dried with sodium sulfate. After distillation, 85 g methacryloylthio(3-thiobutane) was obtained (b.p. 62°–66° C. at 0.2–0.3 mbar; yield 69% of theoretical).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of producing a (meth)acryloylthio ester of the formula I

(I)

where R represents hydrogen or methyl, and
$R_1$ represents a phenyl group, substituted phenyl group, a $C_{1-24}$ alkyl group, substituted, $C_{1-24}$ alkyl group or $C_{3-24}$ cyclic alkyl group; comprising reacting
i) a (meth)acrylic acid anhydride (formula II)

(II)

where R is defined above, in an inert organic-waterimmiscible solvent to constitute an organic phase, with
ii) at least the stoichiometric amount of thiol or thiolate of formula III

 (III)

where M represents hydrogen or a metal, and
R$_1$ is defined as above, in aqueous alkaline solution to constitute an aqueous phase.

2. The method of claim 1, wherein R$_1$ represents a phenyl group, or a C$_{1-16}$ alkyl group.

3. The method of claim 1, wherein M is hydrogen or an alkali cation.

4. The method of claim 3, wherein M is sodium or potassium.

5. The method of claim 1, wherein said (meth)acrylic acid anhydride (II) is employed in a stoichiometric molar excess with respect to the compound (III) by a factor of 0.05–0.5.

6. The process of claim 1 wherein subsequent to the reaction the organic phase is separated from the aqueous please and the (meth)acryloylthio ester (I) is recovered from the organic phase.

* * * * *